US006965834B2

(12) United States Patent
Saito et al.

(10) Patent No.: US 6,965,834 B2
(45) Date of Patent: Nov. 15, 2005

(54) STEAM TURBINE SYSTEM INSPECTING METHOD

(75) Inventors: Kazuhiro Saito, Kanagawa-Ken (JP); Kazunari Fujiyama, Kanagawa-Ken (JP); Taiji Hirasawa, Kanagawa-Ken (JP); Satoshi Nagai, Kanagawa-Ken (JP); Toshihiro Fujiwara, Kanagawa-Ken (JP); Hitoshi Kichise, Kanagawa-Ken (JP); Hirotsugu Kodama, Tokyo (JP); Mitsuyoshi Okazaki, Saitama-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 230 days.

(21) Appl. No.: 10/681,165

(22) Filed: Oct. 9, 2003

(65) Prior Publication Data

US 2004/0128109 A1   Jul. 1, 2004

(30) Foreign Application Priority Data

Oct. 10, 2002 (JP) ............................. 2002-297068

(51) Int. Cl.[7] ........................................... G06F 19/00
(52) U.S. Cl. ........................................ 702/35; 73/627
(58) Field of Search .................... 702/33–35, 81–82, 702/84; 73/592, 865.8, 627; 348/125

(56) References Cited

U.S. PATENT DOCUMENTS

| 4,680,470 A | * | 7/1987 | Heald ...................... 250/358.1 |
| 5,164,826 A | | 11/1992 | Dailey |
| 6,487,922 B1 | * | 12/2002 | Bauer et al. ............... 73/865.8 |

* cited by examiner

Primary Examiner—John Barlow
Assistant Examiner—Cindy Khuu
(74) Attorney, Agent, or Firm—Finnegan, Henderson, Farabow, Garrett & Dunner, L.L.P.

(57) ABSTRACT

The present invention provides a method of inspecting a target component part (e.g., valve casing) of an apparatus (e.g., steam control valve) included in a steam turbine system. When a time period in a range of 24 to 100 hours passes from the shutting-down of the turbine system, or before a temperature of an atmosphere surrounding the component part is lowered to 100° C., the width of the opening of the crack formed in the component part or a clearance relating to the component part is measured without disassembling the target component part and an enclosing member (e.g., valve casing) from the apparatus. As the measurement is performed when a thermal stress is induced in the component parts or when the temperature distribution is wide, the risk level of the crack or the clearance is determined accurately.

10 Claims, 6 Drawing Sheets

STEAM TURBINE SYSTEM INSPECTING METHOD

BACKGROUND OF THE INVENTION

1. Field of the Invention

The present invention relates to a method of inspecting a component part of an apparatus included in a steam turbine system.

2. Description of the Related Art

A steam turbine always has a possibility that damage occurs due to the aged degradation and erosion of the component parts. In order to maintain the rated performance and efficiency of the turbine, the turbine is inspected periodically to find damaged parts before the parts are damaged seriously.

Principal component parts to be inspected periodically of the steam turbine include moving blades, nozzles, a rotor, casings of high and medium-pressure stage turbines, valves, and steam pipes. Most defects that occur in those principal parts are cracks and fissures due to fatigue or creep, and thickness reduction and breakage due to erosion. Although it is possible that cracks are formed in portions of an outer surface of a turbine casing on which stress is concentrated, most defects occur on surfaces of the component parts exposed to high temperature and steam and thus subjected to quality degradation, creep, thermal fatigue and erosion.

In inspecting a turbine, the upper half casing is removed, and radial and axial clearances between the rotating and stationary component parts are measured. Then the rotor is hoisted, the rotor, the moving blades, the nozzles and the turbine casing are visually inspected for defects, erosion and cracks, and non-destructive inspection such as PT, MT or UT is carried out. Then it is judged whether the component parts should be repaired or replaced, and they are repaired or replaced if necessary. Then, the rotor is returned into the turbine casing, clearances are measured and adjusted, and the upper half casing is set in place.

When defects (e.g., cracks) are found by inspection in component parts which permit of no defects therein, such as rotating parts, it is usual to take measures immediately to eliminate the defects.

When defects are found by visual inspection in a non-rotating component part, such as a turbine casing or a valve casing, the risk of possible troubles is determined based on data on the degree of degradation of the material and stress distributions in the component part. The degree of degradation of the material is examined through replication, hardness measurement or electrochemical test. The stress distribution is estimated by minute analysis using a FEM (finite element method).

In detail, when a defect is found by inspection and then the size and shape of the defect are measured, consumed life (i.e., creep damage and/or fatigue damage accumulated in the damaged parts) of the damaged part is calculated based on the record of operation of the damaged part and the degree of degradation of the material examined through the non-destructive test. Based on the calculation result, remaining life, which is dependent on the possibility of formation and development of cracks, of the damaged part is estimated by using the factors including: temperature/stress probability distribution determined by the finite element method based on the shape and operating condition of the member; future mode of operation; and the aged degradation of the material. Then, the condition of the damaged part is determined based on the estimated remaining life, the risk level of the defect is determined and countermeasures to eliminate the defect are planed.

However, if the turbine is disassembled for inspection, a considerably long inspection time is necessary, that is, it takes about thirty days from shutdown of the turbine to the operation of the turbine at the rated temperature after restart of the turbine.

Moreover, estimation of stress distribution for the determination of the risk level of the defect takes time, and the estimated stress distribution is greatly dependent on a temperature boundary condition used by analysis by a FEM. Since most plants do not have sufficient data, and hence the accuracy of analysis by a FEM is not necessarily satisfactory. Consequently, the accuracy of determination of the risk level of a defect, such as a crack, found by visual inspection is limited.

In order to shorten the inspection time, a non-disassembling inspection method has been proposed. The method does not open the casing and inserts a fiberscope or a CCD camera through the flanged end of a steam pipe into the turbine casing. This inspection method omits a step of opening the casing, and a step of adjusting the clearances between the casing and blades, which is inevitable when the turbine casing is opened. In this method, however, the fiberscope or the CCD camera is inserted into the turbine casing for inspection after the temperature of the interior of the turbine casing has dropped near to an ordinary temperature. Thus, this method also takes a considerable long time, and also has the problem on unsatisfactory accuracy of the risk level determination.

SUMMARY OF THE INVENTION

The present invention has been made in view of the foregoing problems and it is therefore an object of the present invention to provide a turbine system inspecting method that can be carried out in a short time period and highly accurately, quickly achieve the determination of the risk level of an abnormality found by inspection.

The inventive concept of the present invention is as follows. In the event that the target component part (i.e., the, component part to be inspected) is that high temperature steam flows therethrough, such as a turbine casing or a valve casing, stresses are induced in the component part due to an internal steam pressure and a temperature distribution. (The stress induced due to the internal steam pressure is referred to as "internal-pressure-related stress", and the stress induced due to the temperature distribution is referred to as "thermal stress" in this specification hereinafter.)

In general, component parts through which high-temperature steam flows of the steam turbine is designed such that the internal-pressure-related stress is lower than the thermal stress in order to limit damage due to creep to the least extent. Thus, the thermal stress has a great effect on the development of cracks in the component parts. Therefore, in order to determine the risk of cracks formed in such component parts accurately, it is very important to know the thermal stress induced in the cracked portion accurately.

If the thermal stress is released, the crack is closed. If the thermal stress induced in the cracked portion is considerably high, the crack is opened. The dimension or the size of the opening of the crack closely relates to the thermal stress induced in the cracked portion. In other words, the thermal stress induced in the cracked portion, which is difficult to calculate accurately only by a FEM, can be estimated with high accuracy based on the dimension or the size of the opening of the crack. Therefore, the risk level of the crack can accurately be determined by examining the dimension or the size of the opening of the crack when a thermal stress is induced in the cracked portion, preferably when a maximum thermal stress induced in the cracked portion.

Generally, a maximum thermal stress is induced in the above component part, such as turbine casing, during starting-up and the shutting-down of the steam turbine system.

The clearance between adjacent component parts (e.g., first stage moving blades and a turbine casing) during operation is a very important parameter that determines the performance and efficiency of the turbine. Similar to the thermal stress as discussed above, the clearance is dependent on thermal expansion distribution in the component parts due to temperature distribution. Therefore, the risk level of the clearance can accurately be determined by measuring the clearance when the temperature of the component parts is distributed in a wide range.

In view of the above, it is advantageous that the inspection is performed when the atmospheric temperature of the internal space of the apparatus (e.g., a turbine and a valve) included in the turbine system is preferably not less than 100° C., more preferably 100° C. to 300° C. It is also preferable that the inspection is performed when a time period in a range of 24 to 100 hours passes from the shutting-down of the turbine system. According to the above, the inspection can be carried out while the temperature distribution is wide enough.

It is advantageous that the component parts are not disassembled. This is because, upon disassembly, the component parts lose most of the thermal stress induced therein, and the clearance cannot be measured. In addition, the disassembly lengthens the inspection time.

Accordingly, the present invention provides a method of inspecting a target component part of an apparatus included in a steam turbine system, the target component part being exposed to steam that flows through a space defined by an enclosing member of the apparatus when the steam turbine system is in normal operation. The method including the steps of: shutting down the steam turbine system which has been in normal operation; obtaining, after shutting down the turbine system, a first data by means of an inspecting device, the first data relating to a dimension of a crack formed in the target component part or relating to a clearance between the target component part and an adjacent component part arranged adjacent to the target component part, wherein the obtaining step is performed when a time period in a range of 24 to 100 hours passes from the shutting-down of the turbine system, or before an atmospheric temperature of the space is lowered to 100° C., and wherein the obtaining step is performed without disassembling the enclosing member and the target component part from the apparatus having the target component part; and judging whether the target component part should be repaired upon comparing the data with a judgmental standard, or comparing an output calculated by applying the data to a predetermined function with a judgmental standard.

The step of obtaining the first data may be performed when the atmospheric temperature of the space is not more than 300° C.

The method may further include a step of obtaining, after the step of obtaining the first data is performed, a second data by means of the inspecting device, the first data relating to a dimension of a crack formed in the target component part or relating to a clearance between the target component part and an adjacent component part arranged adjacent to the target component part, wherein the step of obtaining the second data is performed without disassembling the enclosing member and the target component part from the apparatus having the target component part, and wherein the judging step is performed by comparing at least one of the first data and the second data with a judgmental standard, or comparing an output calculated by applying at least one of the first data and the second data to a predetermined function with a judgmental standard.

The first data relating to the clearance may be the clearance itself, a dimension of an eroded portion in the target component part or said adjacent component part, or a dimension of a scale layer formed on the target component part or said adjacent component part.

The step of obtaining the first data may be performed with the inspecting device being inserted into the space through an insertion path extending through the enclosing member.

In one embodiment, the apparatus included in a steam turbine system is a turbine, and the enclosing element is a turbine casing; and the insertion path comprises a steam pipe for supplying or discharging the steam into or from the turbine when the turbine system is in the normal operation, or an opening exclusively formed in the turbine casing for insertion of the inspecting device.

The inspecting device may comprise an image pick-up device adapted to pick up an image of the target component part. The image pick-up device may be a CCD camera, a fiberscope or the like.

The target component part may be the enclosing member having an inner surface facing the space and an outer surface, and wherein the step of obtaining the first data may be performed with the inspecting device being attached to the outer surface of the enclosing member.

In this case, the inspecting device may comprise a probe of an ultrasonic flaw detection apparatus.

In one embodiment, the apparatus included in the steam turbine system may be a valve for stopping or controlling a flow of the steam, and wherein the enclosing member may be a valve casing.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Preferred embodiments of the present invention will be described with reference to the attached drawings.

The present invention relates to a method of inspecting a target component part (i.e., a component part to be inspected) of an apparatus included in a steam turbine system, the target component part being exposed to steam that flows through a space defined by an enclosing member of the apparatus when the steam turbine system is in normal operation.

Figure 1:
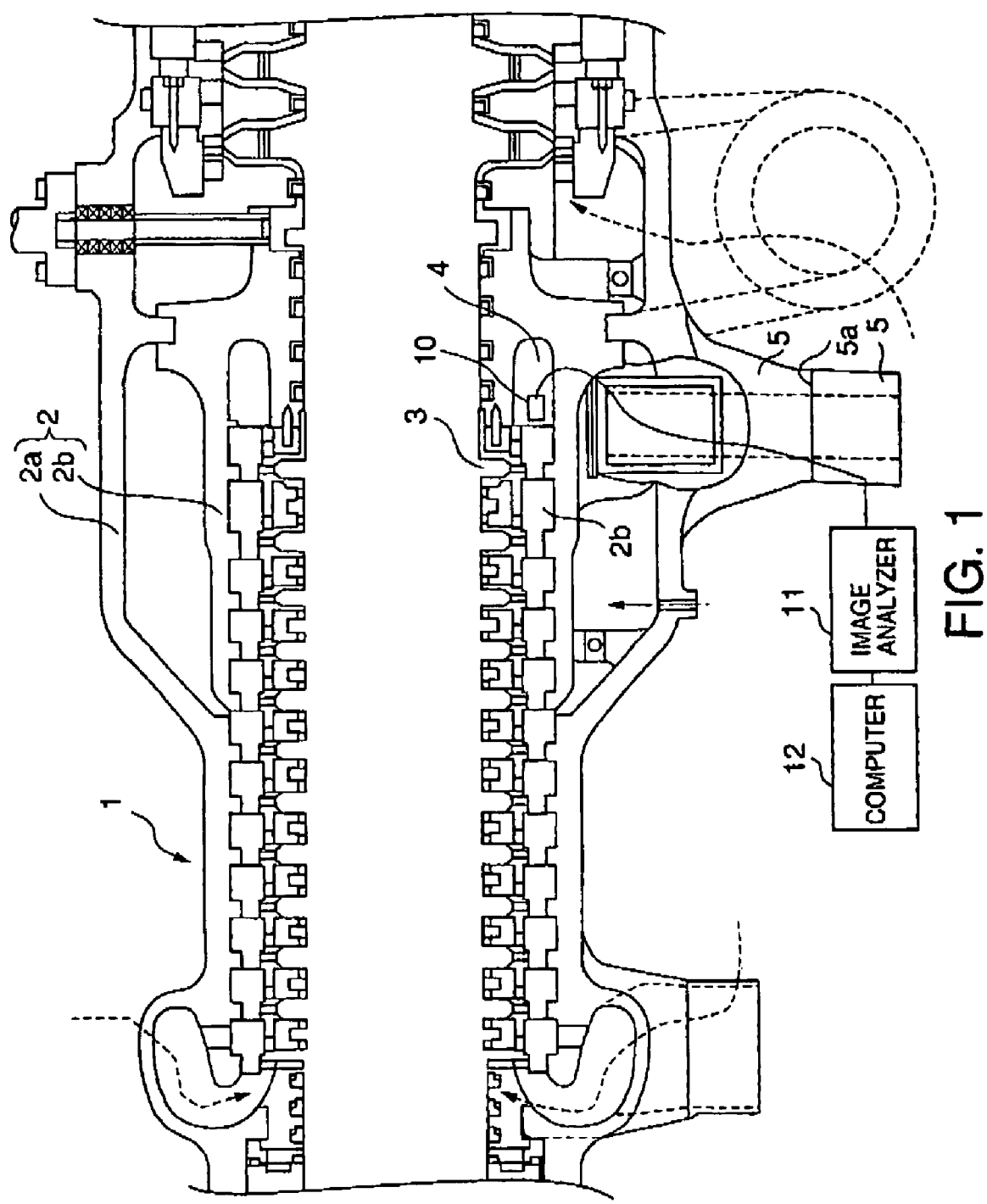
FIG. 1 shows an inspecting device inserted in a steam turbine casing.
Figure 2:
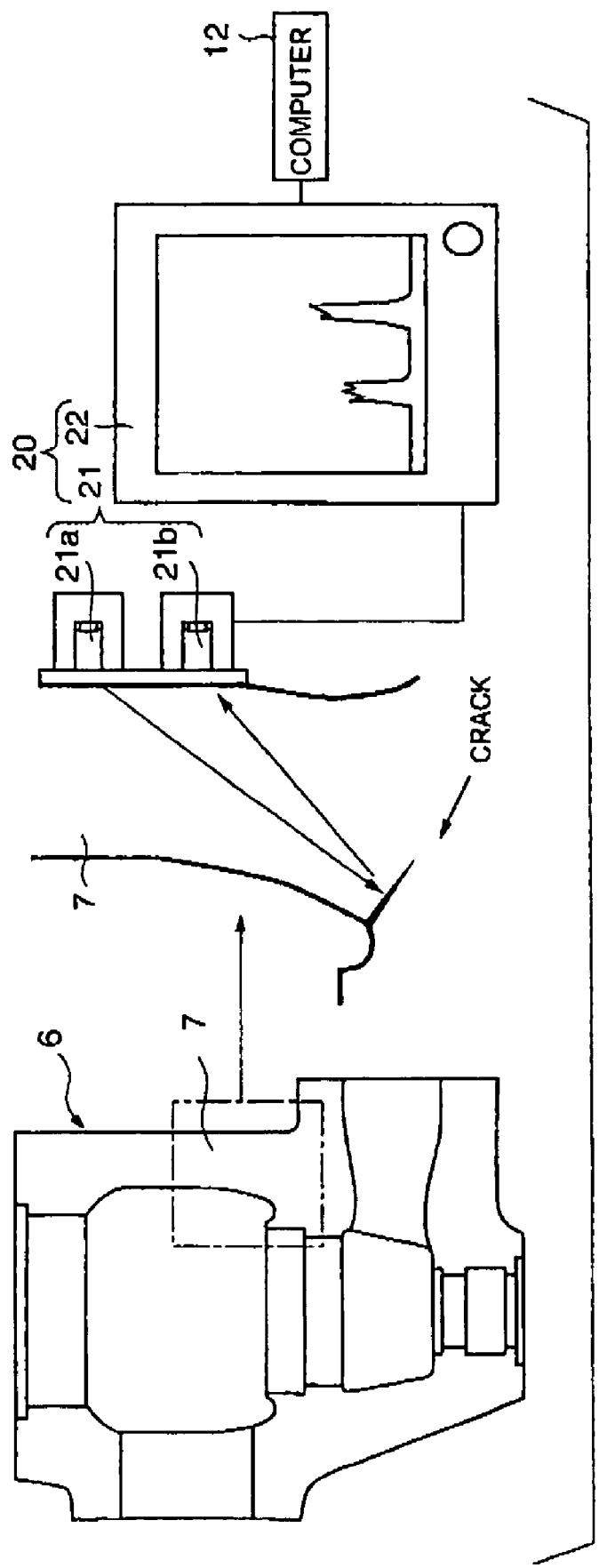
FIG. 2 shows an inspecting device attached to a valve casing.

With reference to FIGS. 1 and 2, the following description will be made for an example in which: the apparatuses are a high-pressure steam turbine having a double-casing structure 2, and a valve 6 for controlling or stopping the flow of the steam (in this embodiment, a main stop valve (MSV)); the target component parts are an inner turbine casing 2b and a moving blade 3 of the high-pressure steam turbine 1, and a valve casing 7 of the valve 6; and the inspecting items are cracks formed in inner side of the inner turbine casing 2b and a valve casing 7, and a clearance between the tip of the moving blade 3 and the inner surface of the inner turbine casing 2b.

The steam turbine system, which has been in normal operation, stops or is shut down.

Then, as shown in FIG. 1, a remote-controlled CCD camera 10 (i.e., an image pickup device) is inserted into an interior space of the turbine and picks up images of several portions of the inner surface of the inner casing when the predetermined time (preferably 24 to 100 hours) has passed from the shutdown of the turbine system, or when an atmospheric temperature of the interior space 4 of the turbine in the vicinity of the target component part is lowered to a predetermined temperature (preferably 100° C. to 300° C.).

Preferably, the CCD camera 10 has a device such as magnet rollers (not shown) that allows the CCD camera 10 to move on surfaces of the component parts of the turbine.

The insertion of the CCD camera 10 is carried out without disassembling the turbine casings 2a and 2b, or overhauling the turbine 1. The CCD camera 10 is inserted into the interior space of the turbine casing 1 from the flanged end 5a of the steam pipe 5 through the steam pipe 5. In this case, the steam pipe 5 is divided for insertion of the CCD camera 10. The insertion route may be any one of those indicated by chain arrows shown in FIG. 1. The turbine may be provided with holes exclusively for insertion of the CCD camera 10, which may be formed in the wall of the steam pipe 5 or the turbine casing 2a, 2b, and which are sealingly closed when the turbine system is in normal operation.

The image data obtained by the CCD camera 10 is sent to an image analyzer 11. If any crack is found, the dimension or size (e.g., width W and/or length L) of the opening of the crack (i.e., crack-opening dimension) is determined by image analysis. Alternatively, the crack-opening dimension may be calculated manually based on the displayed image.

Preferably, a temperature sensor (not shown) is attached to the CCD camera 10 to measure the atmospheric temperature (i.e., inspection temperature) of the interior space 4 of the turbine 1 in the vicinity of the target component part.

The data on the crack-opening dimension and the inspection temperature is sent or inputted to a computer 12. According to a predetermined procedure which will be described later, the computer 12 judges whether the cracked portion should be repaired based on the crack-opening dimension and the inspection temperature.

The CCD camera 10 also picks up images of a gap between adjacent component parts, such as a tip of the moving blade 3 and an inner surface of the inner turbine casing 2b.

The image data is sent to an image analyzer 11. The clearance between the component parts is determined by image analysis. The temperature sensor also measures the atmospheric temperature (i.e., inspection temperature) of the interior space of the turbine in the vicinity of the target component parts.

The data on the clearance and the inspection temperature is sent or inputted to a computer 10. According to a predetermined procedure which will be described later, the computer 10 judges whether the clearance should be adjusted based on the measured clearance and the inspection temperature.

Simultaneously with the inspection by using the CCD camera 10, the inspection of the valve casing 7 is carried out.

As shown in FIG. 2, a remote-controlled probe unit 21 of an ultrasonic flaw detection apparatus 20 (i.e., non-destructive inspection device) is attached onto an outer surface of the valve casing 7. The probe unit 21 has a pair of ultrasonic transducers 21a and 21b, one 21a for emitting an ultrasonic wave and the other 21b for receiving the reflected ultrasonic wave. The probe unit 21 has a device such as magnet rollers (not shown) that allows the probe unit 21 to move on the outer surface of the valve casing 7.

By means of the ultrasonic flaw detection apparatus 20, the dimension of a crack, if any, formed in the valve casing is measured based on the wave pattern shown on a display 22. The data on the crack dimension and the inspection temperature is sent or inputted to the computer 12.

According to a predetermined procedure which will be described later, the computer 12 judges whether the cracked portion should be repaired based on the crack dimension and the measured temperature. As it is difficult to directly measure the atmospheric temperature of the interior space of the valve casing 7, the atmospheric temperature may be estimated or calculated based on the temperature of the outer surface of the valve casing.

If it is judged that the cracked portion should be repaired, or if it is judged that the clearance should be adjusted, the outer and inner casings 2a and 2b of the turbine 1 or the valve casing 7 are disassembled. Then, the cracked portion is repaired by a suitable conventional method, or the clearance is adjusted by a suitable conventional method.

On the contrary, if it is judged that the repairing of the cracked portion and the clearance adjustment are not necessary, the turbine 1 and valve 6 are not overhauled and the turbine system may be restarted immediately. In this case, the maintenance time is shortened drastically.

Figure 3A:
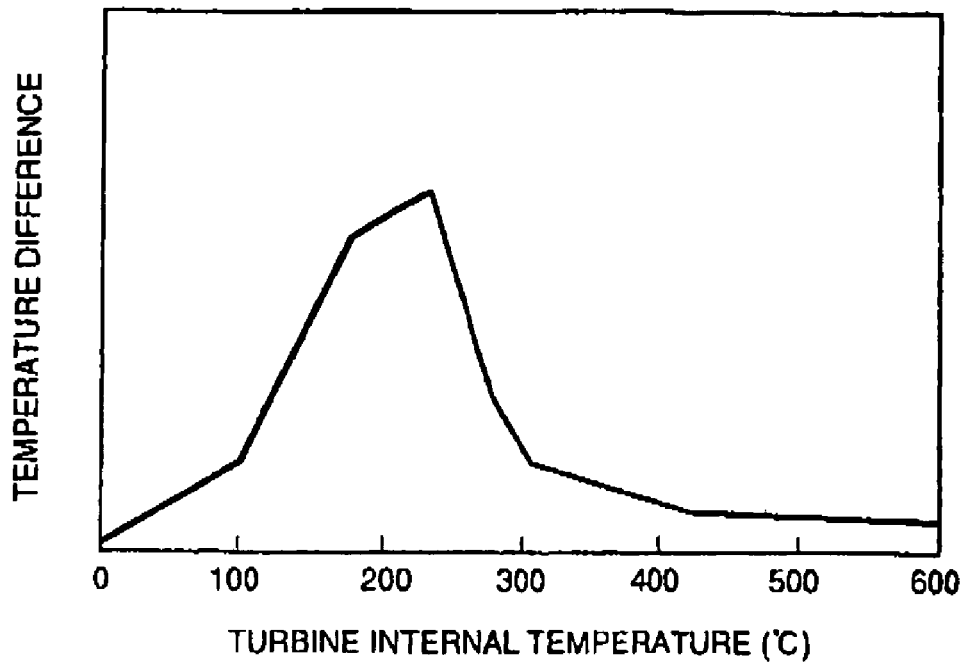
FIG. 3A is a graph showing the dependence of temperature difference between the interior and the exterior of a turbine casing on turbine internal temperature.
Figure 3B:
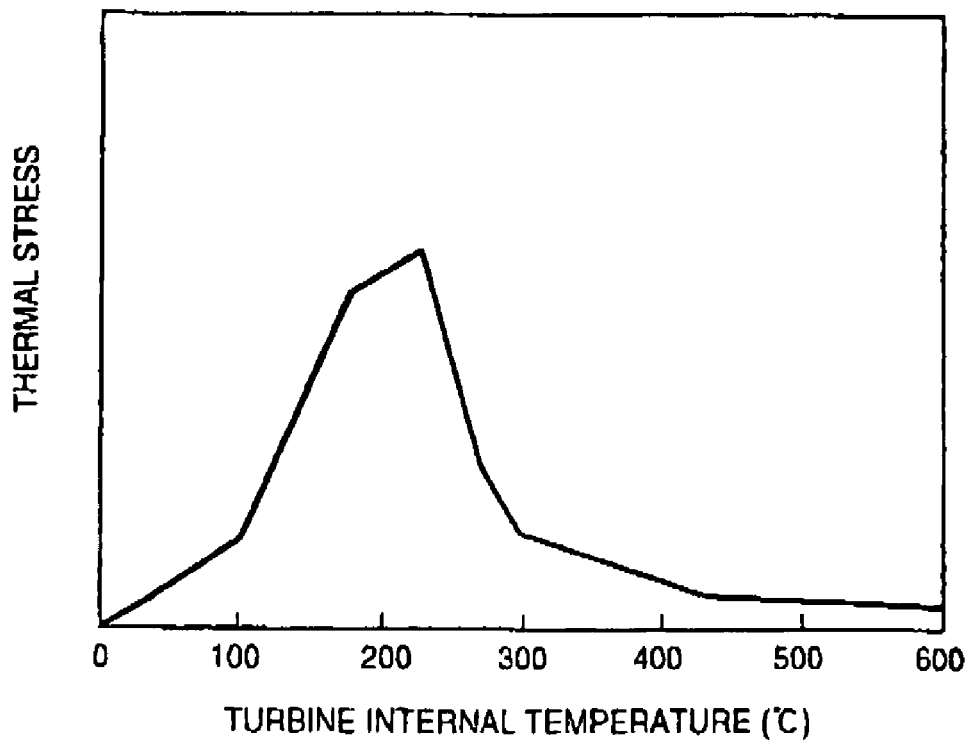
FIG. 3B is a graph showing the dependence of thermal stress on turbine internal temperature.

FIG. 3A is a graph showing the dependence of temperature difference between the interior and the exterior of a turbine casing on turbine internal temperature (i.e., atmospheric temperature of the interior space of the turbine casing where steam flows) after shutting-down of the turbine system. FIG. 3B is a graph showing the dependence of thermal stress on turbine internal temperature. The temperature difference and the thermal stress are high when the turbine internal temperature is in the range of 100° C. to 300° C. The changes in the temperature difference and in the thermal stress shows similar tendency after starting-up of the turbine system.

Figure 4:
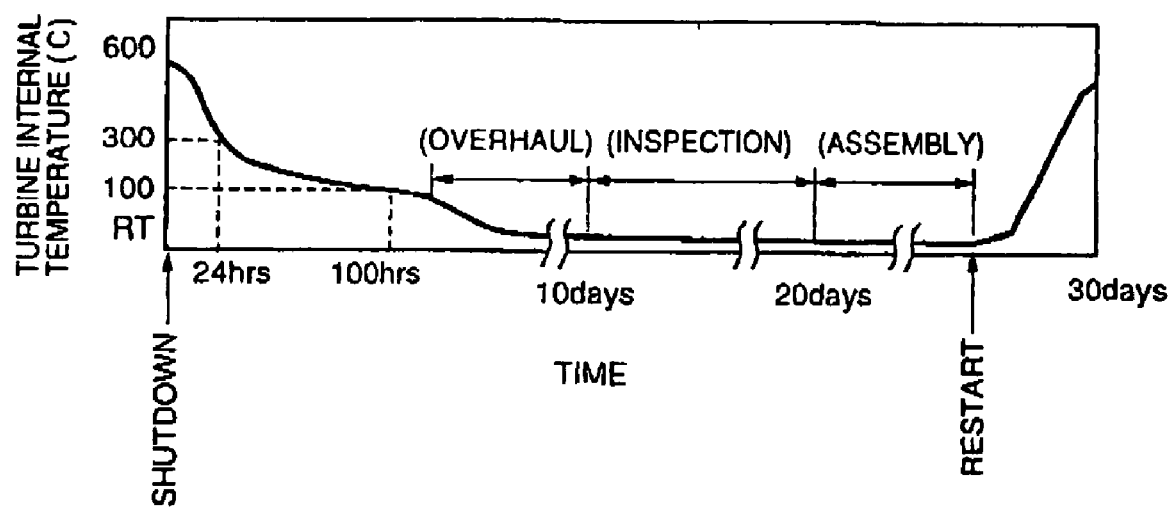
FIG. 4 is a graph showing the change in temperature after shutting down the turbine, and also showing maintenance schedule of the conventional method.

As shown in FIG. 4, the turbine internal temperature is lowered to about 300° C. when about 24 hours has elapsed from the shutting-down of the turbine system, and is lowered to about 100° C. when about 100 hours has elapsed from the shutting-down of the turbine system.

Similarly, the change in the clearance is maximal when the turbine internal temperature is in the range of 100° C. to 300° C. The valve casing shows a similar tendency.

Therefore, the inspection is preferably performed when the turbine internal temperature is in the range of 100° C. to 300° C., or when a time period in a range of 24 to 100 hours passes from the shutting-down of the turbine system.

Figure 5:
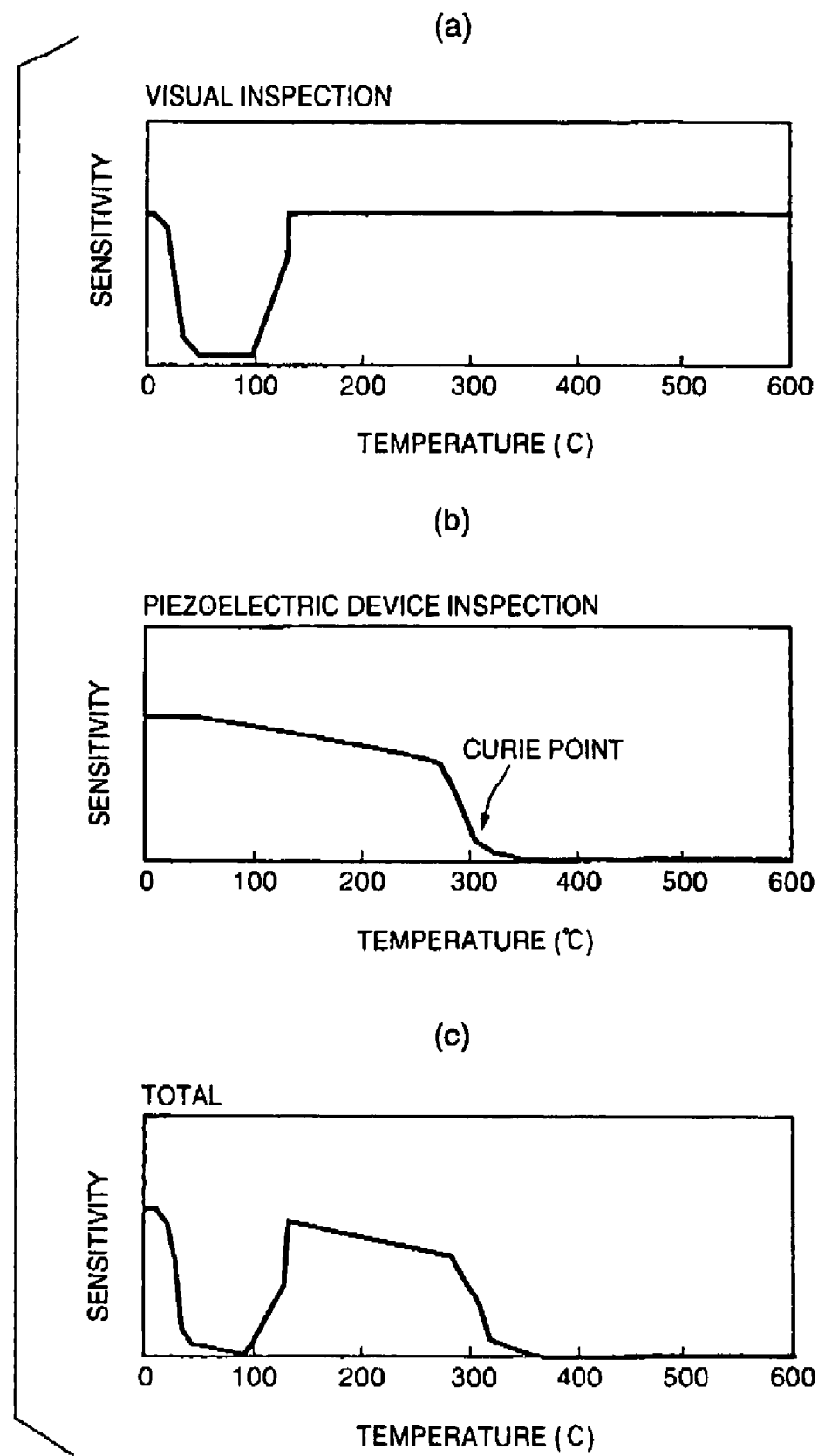
FIGS. 5($a$), ($b$) and ($c$) are graphs showing the dependence of sensitivity on temperature in visual inspection using a CCD camera or a fiberscope, inspection using a piezoelectric device (i.e., the probe of the ultrasonic flow detection apparatus), and inspection using both visual observation and a piezoelectric device, respectively.

However, the inspection temperature should be decided based on the temperature dependence of the performance of the inspection devices. FIG. 5(a), (b) and (c) are graphs showing the dependence of sensitivity on temperature in visual inspection using a CCD camera or a fiberscope, inspection using a piezoelectric device (i.e., the probe of the ultrasonic flow detection apparatus), and inspection using both visual observation and a piezoelectric device. When a CCD camera is used, dew condenses on the lens of the CCD camera at temperatures not higher than 100° C. to lower sensitivity. The measuring accuracy of a piezoelectric device drops sharply when the temperature increases beyond the Curie point.

Therefore, if the CCD camera is used for the inspection, the inspection temperature should be not lower than 100° C. If the piezoelectric device is used for the inspection, the inspection temperature should be not higher than the Curie point, typically 300° C. If both devices are used, the temperature should be in the range of 100° C. to 300° C., as shown in FIG. 5(c). However, some piezoelectric devices have Curie points higher than 300° C. In such a case, the inspection temperature may be higher than 300° C.

Next, the judgment based on the measurement will be described.

First Judgment Method

The first judgment method is a very simple method. The computer includes a database in which a judgmental standard is stored, and judges whether the component part should be repaired based on the judgmental standard.

Figure 6:
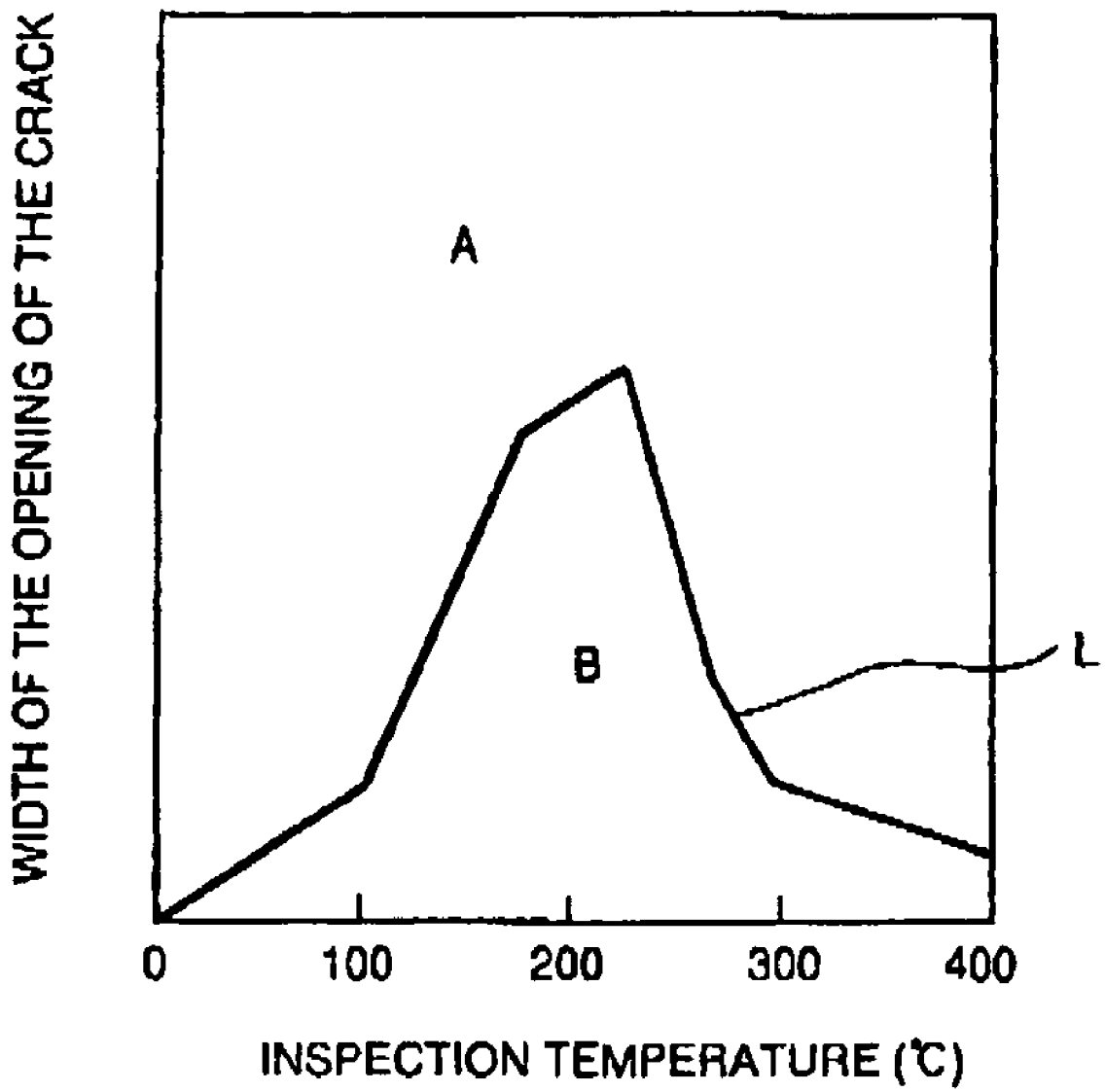
FIG. 6 is a graph showing a judgment standard used for judging whether the cracked portion should be repaired.

The graph of FIG. 6 shows the judgmental standard. The data on the width of the opening of the crack (hereinafter referred to as "crack-opening width") and the inspection temperature is plotted on the graph. If the plot is in area A above line L, it is judged that the crack portion should be repaired. If the plot is in area B below line L, it is judged that the crack portion needs not be repaired. The, graph may be prepared by minute analysis using a FEM.

The judgmental standard for clearance may be prepared in a similar manner.

Second Judgment Method

When the computer received the data on the crack-opening width and the inspection temperature (e.g., 150° C.), the computer estimated a crack-opening width and the thermal stress induced in the cracked portion at a specific temperature (e.g., 280° C.) at which a maximum thermal stress induced in the cracked portion. The computer applies the estimated thermal stress to a loading endurance limit diagrams for the material forming the cracked portion stored in the computer, in order to estimate the remaining life of the cracked portion based on the total operation time and/or the shutting-down and starting-up times of the turbine system. If the remaining life is not enough, the computer judges that the cracked portion should be repaired.

The maximum thermal stress may be estimated or calculated by using simplified models, such as a cylindrical-shaped model for turbine casing, which are well-known in the technical field of materials and mechanics. Alternatively, the estimation may be done by minute analysis by using a FEM. In this case, the calculation result by the FEM prepared beforehand may be corrected based on the result of the measurement. For example, if the crack-opening width at the inspection temperature calculated by the FEM is 1 mm and the measured crack width at the inspection temperature is 1.5 mm, the maximum thermal stress calculated by the FEM is corrected by multiplying the calculated thermal stress by a correction coefficient such as 1.5. Other correction methods that correct an estimated or calculated value by using an actual value may be used.

In the event that the inspection item is the clearance between the component parts, when the computer received the data on the clearance and the inspection temperature (e.g., 150° C.), the computer estimated the clearance at a specific temperature. The specific temperature may be a first temperature of about 280° C., for example, at which the temperature distribution is widest. The specific temperature may be a second temperature, of about 550° C., for example, which is a rated temperature of the turbine, i.e., a temperature of the turbine when the turbine is in normal operation. The estimation may be done in the same manner as that in estimating the thermal stress. The computer judges whether or not the clearance at the specific temperature result in any trouble of the turbine or in reduction of the efficiency of the turbine. If it is judged that any problem exists, the clearance is adjusted by any suitable method.

Third Judgment Method

This method uses at least two data obtained at different inspection temperatures. For example, the crack-opening width at a first inspection temperature of about 150° C. and the crack-opening width at a second inspection temperature of about 250° C. are measured. Thus, the dependence of parameter of defects, such as the crack-opening width, on temperature can be determined by using temperature difference and the measured data. The crack-opening width at temperatures beyond the range of the first inspection temperature to the second inspection temperature, and the crack width at temperatures between the first and the second inspection temperatures can be estimated by interpolation or extrapolation based on the plurality of inspection temperatures. This method may be applied to the evaluation of the clearances measured at two or more different inspection temperatures.

By using the estimated data by interpolation or extrapolation, the computer may judge whether repairing of the crack or clearance adjustment is necessary in the same manner as that in the second judgment method.

Only one of said at least two data may be used. For example, the judgment is done based on the largest or smallest crack-opening width, or the largest or smallest clearance. In this case, the judgment may be done in the same manner as that in the first or the second judgment method.

According to the present invention, as the inspection is performed when a relatively high thermal stress is induced in the component part(s) or temperature distribution is relatively wide, accurate evaluation of the thermal stress or the clearance, which is difficult by the conventional method, is possible. Therefore, it is possible to appropriately judge whether or not maintenance is necessary.

The present invention is not limited to the aforementioned embodiments. The inspection devices are not limited to the CCD camera and the ultrasonic flaw detection apparatus, and any other suitable inspection devices may be used. For example, a fiberscope may be used for visual inspection instead of the CCD camera. A device for laser UT or AE (acoustic emission) test may be used. The probe unit of the ultrasonic flaw detection device may be inserted into the interior space of the turbine casing to measure the size of the crack.

The inspection item is not limited to those as mentioned above. For example, fastening bolts for the valve casing may be inspected.

Moving blades or any other critical parts, to which a relatively low thermal stress is induced or in which temperature distribution is relatively narrow, may be inspected for cracks or erosion simultaneously with the inspection of such parts to which high thermal stress is induced or in which temperature distribution is wide, such as the turbine or valve casing.

What is claimed is:

1. A method of inspecting a target component part of an apparatus included in a steam turbine system, the target component part being exposed to steam that flows through a space defined by an enclosing member of the apparatus when the steam turbine system is in normal operation, said method comprising the steps of:

shutting down the steam turbine system which has been in normal operation;

obtaining, after shutting down the turbine system, a first data by means of an inspecting device, the first data relating to a dimension of a crack formed in the target component part or relating to a clearance between the target component part and an adjacent component part arranged adjacent to the target component part, wherein the obtaining step is performed when a time period in a range of 24 to 100 hours passes from the shutting-down of the turbine system, or before an atmospheric temperature of the space is lowered to 100° C., and wherein the obtaining step is performed without disassembling the enclosing member and the target component part from the apparatus having the target component part; and judging whether the target component part should be repaired upon comparing the first data with a judgmental standard, or comparing an output calculated by applying the first data to a predetermined function with a judgmental standard.

2. The method according to claim 1, wherein the step of obtaining the first data is performed when the atmospheric temperature of the space is not higher than 300° C.

3. The method according to claim 1 further comprising a step of obtaining, after the step of obtaining the first data is performed, a second data by means of the inspecting device, the first data relating to a dimension of a crack formed in the target component part or relating to a clearance between the target component part and an adjacent component part arranged adjacent to the target component part, wherein the step of obtaining the second data is performed without disassembling the enclosing member and the target component part from the apparatus having the target component part, and wherein the judging step is performed by comparing at least one of the first data and the second data with a judgmental standard, or comparing an output calculated by applying at least one of the first data and the second data to a predetermined function with a judgmental standard.

4. The method according to claim 1, wherein the first data relating to the clearance is the clearance itself, a dimension of an eroded portion in the target component part or said adjacent component part, or a dimension of a scale layer formed on the target component part or said adjacent component part.

5. The method according to claim 1, wherein the step of obtaining the first data is performed with the inspecting device being inserted into the space through an insertion path extending through the enclosing member.

6. The method according to claim 5, wherein:

the apparatus included in a steam turbine system is a turbine, and the enclosing element is a turbine casing; and the insertion path comprises a steam pipe for supplying or discharging the steam into or from the turbine when the turbine system is in the normal operation, or an opening formed in the turbine casing exclusively for insertion of the inspecting device.

7. The method according to claim 1, wherein the inspecting device comprises an image pick-up device adapted, to, pick up an image of the target component part.

8. The method according to claim 1, wherein the target component part is the enclosing member having an inner surface facing the space and an outer surface; and wherein the step of obtaining the first data is performed with the inspecting device being attached to the outer surface of the enclosing member.

9. The method according to claim 8, wherein the inspecting device comprises a probe of an ultrasonic flaw detection apparatus.

10. The method according to claim 8, wherein the apparatus included in the steam turbine system is a valve for stopping or controlling a flow of the steam, and wherein the enclosing member is a valve casing.

* * * * *